United States Patent
Salminen

(10) Patent No.: US 6,499,484 B1
(45) Date of Patent: Dec. 31, 2002

(54) CRUCIAL LIGAMENTS LOADING DEVICE

(75) Inventor: Heikki Veikko Salminen, Vantaa (FI)

(73) Assignee: Koninklijke Philips Electronics, N.V., Eindhoven (NL)

(*) Notice: Subject to any disclaimer, the term of this patent is extended or adjusted under 35 U.S.C. 154(b) by 0 days.

(21) Appl. No.: 09/742,597

(22) Filed: Dec. 21, 2000

(51) Int. Cl.[7] ............................................... A61G 15/00
(52) U.S. Cl. ..................................... 128/845; 128/882
(58) Field of Search ............................... 128/845, 846, 128/869, 870, 882; 602/23, 32, 36, 40; 5/648, 650

(56) References Cited

U.S. PATENT DOCUMENTS

| | | | |
|---|---|---|---|
| 4,232,681 A | * 11/1980 | Tulaszewski | 128/882 |
| 4,323,080 A | * 4/1982 | Melhart | 128/882 |
| 4,407,277 A | * 10/1983 | Ellison | 128/882 |
| 4,984,774 A | 1/1991 | Zupancic et al. | 324/318 |
| 5,007,425 A | 4/1991 | Vanek et al. | 324/318 |

OTHER PUBLICATIONS

"Instrumented Measurement of Antior Knee Laxity in Patients with Acute Anterior Cruciate Ligament Disruption", Daniel, et al., The American Journal of Sports Medicine, vol. 13, No. 6, pp. 401–407.

\* cited by examiner

*Primary Examiner*—Michael A. Brown
(74) *Attorney, Agent, or Firm*—Fay, Sharp, Fagan, Minnich & McKee, LLP

(57) ABSTRACT

A ligament loading device (50) is used in conjunction with an MRI apparatus to image damaged ligaments in the knee. The leg of a patient is strapped into a thigh harness (70) and a lower leg harness (74) with the knee lying over a point (72) in the imaging region of the imager. The thigh harness (70) is fixed, but the lower leg harness (74) rotates about a central pivot point (72) to select an angle for the leg. Pressure devices (84a, 84b) such as sacs or bellows apply pressure to the thigh in one direction transverse to the thigh. Pressure devices (100a, 100b) apply pressure to the lower leg in an opposing direction transverse to the lower leg in order to move the bones of the knee apart to facilitate imaging of the ligaments. It is also possible to inspect and measure the movement of the bones using the device in conjunction with an MRI apparatus. A switch (108) selects between two pressure applying modes, both of which move the bones of the knee apart, but in opposite directions. Pressure is applied with a manual bulb (103) so that a diagnostician can physically feel the amount of pressure that is being applied to the patient's knee.

14 Claims, 2 Drawing Sheets

CRUCIAL LIGAMENTS LOADING DEVICE

BACKGROUND OF THE INVENTION

The present invention relates to the diagnostic imaging arts. It finds particular application in conjunction with open MRI systems when imaging the ligaments of the knee and will be described with particular reference thereto. It will be appreciated, however, that the present invention is also useful in conjunction with X-ray, CT, and other imaging modalities.

In magnetic resonance imaging, a uniform main magnetic field is created through an examination region in which a subject to be examined is disposed. With open magnetic resonance systems, the main magnetic field is generated vertically, between upper and lower pole pieces. A series of radio frequency (RF) pulses and magnetic field gradients are applied to the examination region to excite and manipulate magnetic resonances. Gradient magnetic fields are conventionally applied to encode spatial position and other information in the excited resonance.

When a patient injures his knee, doctors are often interested in the damage the ligaments of the knee have sustained. Unfortunately, the ligaments of the body fit snugly against bones, and as a result, are hard to image using non-invasive imaging techniques. In order to achieve acceptable contrast between the ligament to be imaged and the surrounding tissue, the bones of the knee are moved away from the ligaments.

When using magnetic resonance imaging, the subject remains still during the examination. The main magnetic field is encoded with three dimensional gradient fields that precisely map the imaging area. It is important to have the same region of the subject in the same imaging area throughout the whole imaging process. If the subject moves during imaging, then the parts of the body being imaged will correspond to the wrong spacial position and the resultant image will be an incorrect, double-exposure or blurred representation of the anatomy of the subject. Consequently, the region of the patient being imaged should remain still during the process.

Magnetic resonance compatible fixtures of nylon or aluminum and foam pads have been used to hold a patient's knee at a selected angle during imaging. However, such fixtures and pads only limit or prohibit movement. They are not designed to apply anterior or posterior loading.

A device attributed to M. L. Stone et al as described in the *American Journal of Sports Medicine,* 13:401–407, 1985 Was designed to provide loading on the crucial ligaments. However, the device was not MRI compatible. The patient's knee and foot were supported by an anvil or pivot block and a foot stop block, respectively. The arthometer was strapped to the calf with a tibial sensor pressed against the tibia and a patella sensor pressed against an end of the patella. The operator gripped a force handle on the top of the arthometer with one hand and the patella sensor in the other. In one mode, the operator pulled up on the handle and pushed down on the patella sensor until a gauge or audio signal indicated 7 kg or 9 kg of force. The arthometer was unable to increase the forces on the knee in small, accurate steps. Moreover, it was unsuited to imaging the knee at a series of incremental loading steps.

The present invention provides a new and improved method and apparatus that overcomes the above referenced problems and others.

SUMMARY OF THE INVENTION

In accordance with one aspect of the present invention, an MRI scanner generates a main magnetic field through an imaging region where a subject is disposed. The scanner encodes dipoles in the subject by superimposing gradient fields on the main magnetic field. Magnetic resonance in the selected dipoles is excited and detected by radio-frequency coils and processed into an image representation of the selected area of the subject.

In accordance with another aspect of the present invention, a ligament loading device is disposed in the imaging region which secures the leg of a patient during imaging. The device has the ability to apply anterior/posterior pressure to the patient's leg for the purpose of separating the bones of the knee to make the ligaments of the knee more visible for imaging.

In accordance with a more limited aspect of the present invention, the ligament loading device applies pressure to the patient's leg through the use of operator controlled pneumatic sacs which inflate and cause movable plates to put pressure on the patient's leg. In this manner the operator can feel how much pressure is being put on the leg.

In accordance with another aspect present invention, a method of magnetic resonance imaging is provided where the leg of a patient is disposed in a ligament loading device, a main magnetic field is generated in the region, pressure is applied to the upper and lower portion of the leg in opposing directions, magnetic resonance is excited in the region, the magnetic resonance signals are received, demodulated, and processed into an image representation of the patient's knee.

In accordance with a more limited aspect of the present invention, multiple such images are taken at varying pressures and animated in sequence to yield a cinematographic representation of the patient's knee.

One advantage of the present invention is that it is MRI compatible.

Another advantage of the present invention is that it firmly fixes the knee for imaging.

Another advantage of the present invention is that the amount of force applied is easily limited to safe levels.

Another advantage of the present invention is that it allows the force applied to be read numerically.

Another advantage of the present invention is that it allows the physician to physically feel the amount of force being applied.

Another advantage of the present invention is that it allows for diagnostic imaging of the knee injury without radiation.

Another advantage of the present invention is that it allows for multi-frame imaging over a range of pressures resulting in a cinematographic representation.

Yet another advantage of the present invention is that it is of simple design and low maintenance.

Still further benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENT

Figure 1:
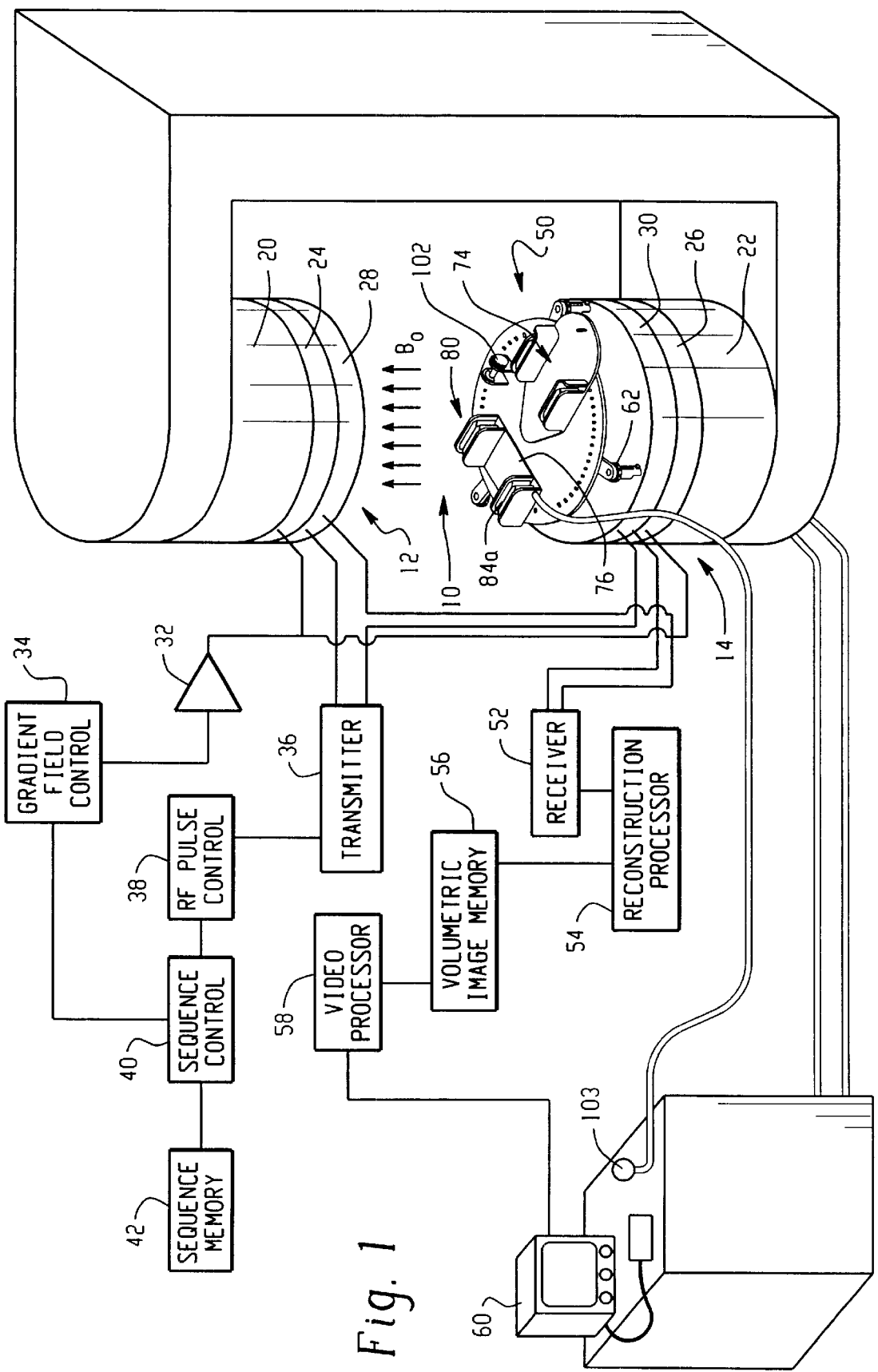
FIG. 1 is a diagrammatic illustration of a magnetic resonance imaging system in accordance with the present invention.

With reference to FIG. 1, in an open MRI system, an imaging region 10 is defined between an upper pole assembly 12 and a lower pole assembly 14. It is to be appreciated that the open MRI apparatus may have a variety of pole pieces or, in some instances, no pole pieces at all. Optionally, a ferrous flux return path is provided between the pole assemblies remote from the imaging region 10. A pair of annular resistive or super-conducting magnets surround upper and lower pole pieces 20, 22 generating a temporally constant, main magnetic field $B_o$ through the imaging region 10. Permanent magnets and active magnets mounted at other positions are also contemplated.

For imaging, magnetic field gradient coils 24, 26 are disposed on opposite sides of the imaging region 10 adjacent the pole pieces 20, 22. In the preferred embodiment, the gradient coils 24, 26 are planar coil constructions which are connected by gradient amplifiers 32 to a gradient magnetic field controller 34. The gradient magnetic field controller 34 causes current pulses which are applied to the gradient coils such that gradient magnetic fields are superimposed on the temporally constant and uniform field $B_o$ across the imaging region 10. The gradient fields are typically generated along a longitudinal or z-axis, a vertical or y-axis and a transverse or x-axis.

In order to excite magnetic resonance in selected dipoles of a subject disposed in the imaging region 10, radio frequency coils 28, 30 are disposed between the gradient coils 24, 26 and the imaging region 10. At least one radio frequency transmitter 36, preferably a digital transmitter, causes the radio frequency coils to transmit radio frequency pulses requested by a radio frequency pulse controller 38 into the imaging region 10. A sequence controller 40, under operator control, retrieves an imaging sequence from an sequence memory 42. The sequence controller 40 provides the selected sequence information to the gradient controller 34 and the radio frequency pulse controller 38 such that radio frequency and gradient magnetic field pulses in accordance with the selected sequence are generated. Typically, the radio frequency coils 28, 30 are general purpose coils and are operable in both transmit and receive modes. Alternately, surface or local coils are provided.

Magnetic resonance signals picked up by the radio frequency coils 28, 30 are demodulated by one or more receivers 52, preferably digital receivers. The digitized signals are processed by a reconstruction processor 54 into volumetric or other image representations which are stored in a volumetric image memory 56. A video processor 58, under operator control, withdraws selected image data from the volume memory 56 and formats it into appropriate data for display on a human readable display 60, such as a video monitor, active matrix monitor, liquid crystal display, or the like.

A removable ligament loading device 50 is disposed in the imaging region 10 between the upper pole assembly 12 and the lower pole assembly 14. The ligament loading device 50 is positioned such that when a subject is inserted into the ligament loading device 50, one of the knees of the subject is at or near an isocenter of the imaging region 10. The subject is positioned on his/her side. Once a volume image is generated, the operator can select the viewing direction(s).

Figure 2:
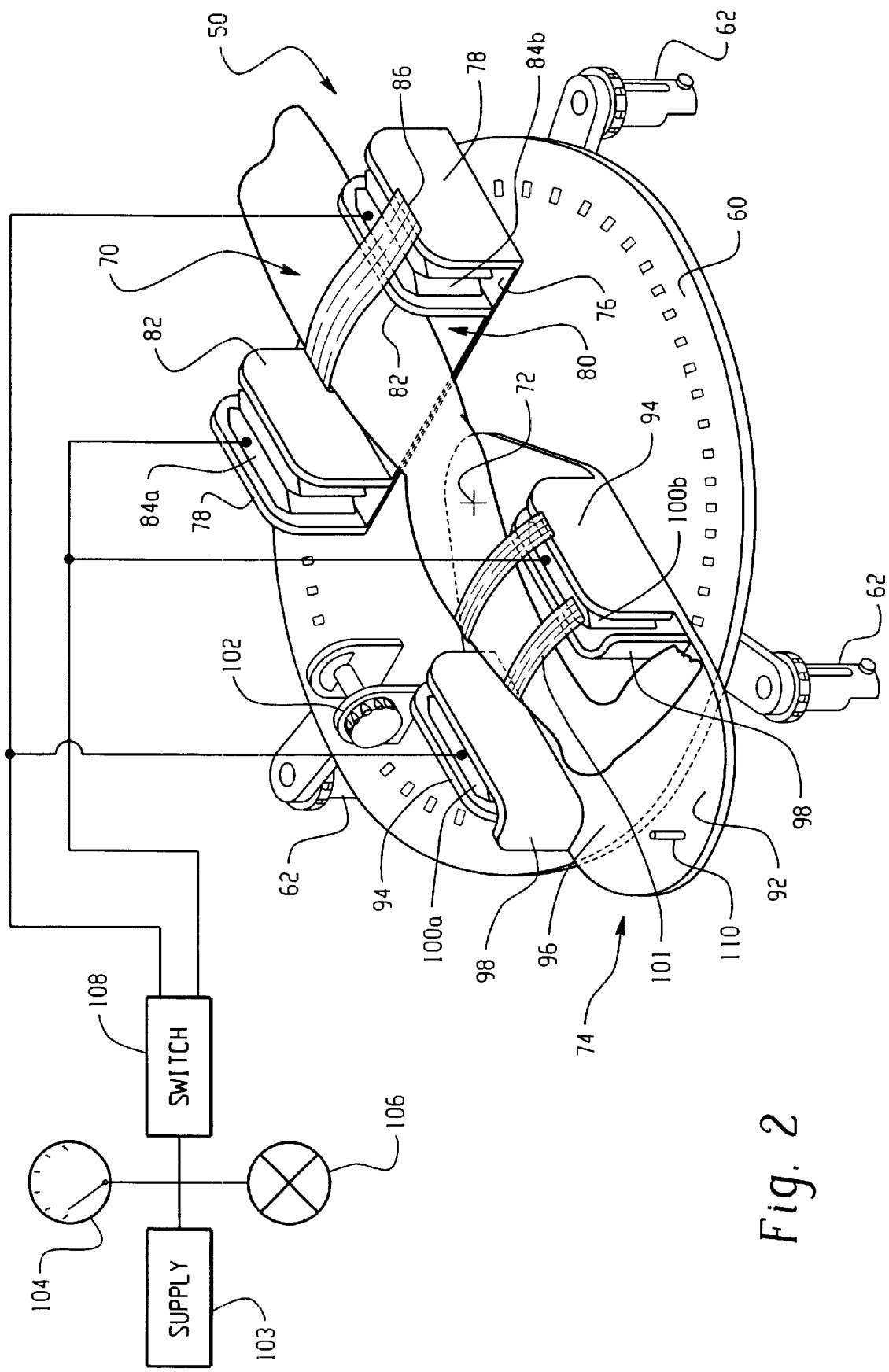
FIG. 2 is a diagrammatic, perspective illustration of a crucial ligament loading device in accordance with the present invention.

With reference to FIG. 2, in the ligament loading device 50, a support platform 60 has downward depending attachment posts 62. The attachment posts 62 secure the ligament loading device 50 to the magnetic resonance apparatus and hold the knee away from the lower pole toward the isocenter.

A fixed thigh harness 70 is disposed at the top of the ligament loading device 50 to receive a leg of a subject in the device. The thigh of the subject is supported by the thigh harness 70 with the knee of the subject resting above a fixed central pivot 72 of the ligament loading device 50. The portion of the leg below the knee is strapped to a mobile lower leg harness 74 which is positioned such that it accepts the lower leg of the subject.

In the preferred embodiment, the thigh harness 70 has a rectangular base 76 with vertical fixed outer plates 78 which are parallel to each other. A slidable thigh pressure carriage 80 has a pair of vertical pressure plates 82 disposed parallel to and between the fixed outer plates 78. In between the movable pressure plates 82 and the fixed outer plates 78 are pneumatically expandable devices such as bellows or sacs 84a, and 84b on each end. The patient's thigh is anchored to the pressure carriage 80 by Velcro straps 86 or other switchable attachments such that the thigh is constrained to move with the pressure carriage 80.

In the preferred embodiment, the lower leg or calf harness 74 has a fixed base 92 and two vertical outer plates 94 which are fixed to said base 92, parallel with respect to each other along the extremities of the base 92. A turning calf pressure carriage 96 has two pressure plates 98 disposed parallel to, and between the fixed outer plates 94. The pressure plates 98 are parallel to each other, perpendicular to the base 92, and between the outer plates 94. The diagnostician manually pivots the lower leg harness 74 by pushing a handle 110. Pneumatic devices 100a and 100b, such as bellows or sacs, are mounted in regions between the movable pressure plates 98 and the fixed outer plates 94. The pneumatic devices 100a and 100b are of expandable volume. One or more Velcro straps 101 or other suitable attachments fixedly position the patient's calf in the calf pressure carriage 96. The lower leg harness 90 is attached to the support platform at one end by the central pivot 72 about which it rotates along the support platform 60.

In the preferred embodiment, the bases of both the thigh harness 70 and the lower leg harness 74 are coplanar, and rest on the support platform 60.

Once the leg of a patient has been disposed in the ligament loading device 50, a diagnostician rotates the lower leg harness 74 about the central pivot 72 until the leg of the subject is at the desired angle for imaging. In the preferred embodiment, the lower leg harness 74 rotates free, but gently locks every 50. A recieving coil is attached at a coil support 102.

For maximum image contrast, or to inspect the movement of the ligament, the bones of the knee are moved away from the ligaments. Once the desired knee angle is achieved, the diagnostician remotely adds pressure to diagonally opposite pneumatic devices 84a and 100b or 84b and 100a with a hand pump 103 while monitoring the pressure on an attached meter 104. This allows the diagnostician to feel the resistance while monitoring the pressure at the same time. A manual pressure release 106 permits the diagnostician to release the pressure. Optionally, the release 106 includes an over pressure valve that prevents pressure from exceeding preset limits. The air from the pump is routed to two of four pneumatic devices which inflate and consequently push their respective pressure carriages 70, 74 against the leg in opposite directions. An anterior-posterior switch 108 is toggled to select which two pneumatic devices 84a and 100b or 84b and 100a are inflated. In one mode, the ligament loading device 50 applies pressure to the anterior of the leg above the knee while applying pressure to the posterior of the leg below the knee. In the other mode, the ligament loading device 50 applies pressure to the posterior of the leg above the knee while applying pressure to the anterior of the leg below the knee. Either mode of pressure application separates the bones of the knee such that the ligaments of the knee are more exposed for imaging. Selection of modes is determined by what ligaments are being studied.

In a ciné mode, images are taken at each of a plurality of pressure increments to obtain a series of images which are displayed in an animated or cine display of the motion of the knee. This action can be useful in studying the effects that certain activities have on the damaged ligaments.

In an alternate embodiment, the pneumatics are replaced by hydraulics. As another alternative, mechanical linkages are used to shift the knee. However, fluid systems are preferred because the diagnostician can feel the pressure as it is being applied.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A ligament loading device comprising:
   (a) a support platform with an attachment system for attaching the platform to an associated apparatus;
   (b) a thigh harness attached to the support platform including:
      a thigh pressure carriage mounted for movement relative to the support platform in a direction transverse to the subject's thigh;
      at least one extensible device for selectively moving the thigh carriage in the transverse direction;
   (c) a lower leg harness pivotally attached to the support platform and including:
      a calf pressure carriage mounted for movement relative to the support platform in a direction transverse to the subject's calf;
      at least one extensible device for selectively moving the calf carriage in the transverse directions.

2. The ligament loading device as set forth in claim 2, wherein:
   the extensible device for moving the thigh carriage includes first and second fluid expansible devices for supplying motive force urging the thigh carriage to move back and forth, respectively, along the transverse direction;
   the extensible device for moving the calf carriage includes third and fourth fluid expansible devices for supplying motive force during the calf carriage to move back and forth, respectively, along the transverse direction;
   a source of fluid pressure; and,
   a fluid pressure control switch for selectively connecting the source of fluid pressure to the first, second, third, and fourth fluid expansible devices.

3. The ligament loading device as set forth in claim 2, wherein the fluid pressure control switch selects between modes in which the fluid expansible devices move the thigh and calf carriages in opposing directions.

4. The ligament loading device as set forth in claim 2, wherein the fluid expansible devices are air-inflated devices.

5. The ligament loading device as set forth in claim 4, wherein the source of fluid pressure includes a hand squeezed bulb, that provides tactile feedback of the supplied pressure.

6. The ligament loading device as set forth in claim 4 further including a barometer which measures the pressure supplied by the source of fluid pressure.

7. The ligament loading device as set forth in claim 1, wherein the extendible devices include pneumatically expandable devices and further including:
   a hand pump for supplying pneumatic pressure to the pneumatically expandable devices.

8. The ligament loading device as set forth in claim 7, wherein the pneumatically expandable devices include one of sacs and bellows.

9. The ligament loading device as set forth in claim 1, wherein the support platform and the thigh harness are constructed of non-ferrous materials.

10. The ligament loading device as set forth in claim 9, wherein the associated apparatus includes a magnetic resonance imaging apparatus.

11. A ligament loading device for use in conjunction with an open field magnetic resonance apparatus comprising:
    (a) pneumatically expansible devices mounted for applying pressure to pressure plates as they expand;
    (b) an air supply for expanding the pneumatically expansible devices;
    (c) an upper limb harness;
    (d) a lower limb harness which is angularly orientable relative to the upper limb harness;
    (e) a source of pneumatic pressure;
    (f) a switch that selectively directs the pneumatic pressure to the pneumatically expansible devices;
    (g) a meter to measure pressure supplied to the pneumatically expansible devices; and,
    (h) a pressure release valve for releasing pressure from the pneumatically expansible devices.

12. The ligament loading device as set forth in claim 10, wherein the pneumatically expansible devices consist of one of air sacs or bellows.

13. The ligament loading device as set forth in claim 10, wherein the source of pneumatic pressure is a manually operated squeeze bulb.

14. The ligament loading device as set forth in claim 10, wherein the pneumatically expansible devices are four in number, the first and second pneumatically expansible devices disposed to the left and right of the upper limb harness respectively, and the third and fourth pneumatically expansible devices disposed to the left and right of the lower limb harness respectively, further including:
   a switch, when set in one position, selects the first and fourth pneumatically expansible devices, and when set in a second position, selects the second and third pneumatically expansible devices.

* * * * *